United States Patent [19]

Ohmori et al.

[11] Patent Number: 5,378,692

[45] Date of Patent: Jan. 3, 1995

[54] METHOD OF LOWERING LIPIDS

[75] Inventors: Shinji Ohmori, Okayama; Kazumi Ogata, Toyonaka; Hideki Tsuruoka, Kawanishi; Takahiro Sakaue, Itami; Yuuichi Isowaki, Settsu; Yasuko Umegaki, Kobe, all of Japan

[73] Assignee: Senju Pharmaceutical Co., Ltd., Osaka, Japan

[21] Appl. No.: 85,875

[22] Filed: Jul. 6, 1993

[30] Foreign Application Priority Data

Jul. 17, 1992 [JP] Japan ............................. 4-190748

[51] Int. Cl.$^6$ ................ A61K 37/00; A61K 31/225; A61K 31/22; A61K 31/195
[52] U.S. Cl. ..................................... 514/19; 514/547; 514/550; 514/551; 514/562; 514/824
[58] Field of Search ................ 514/18, 547, 562, 19, 514/824, 550, 551

[56] References Cited

U.S. PATENT DOCUMENTS

| | | | |
|---|---|---|---|
| 5,081,149 | 1/1992 | Ohmori et al. | 514/534 |
| 5,135,952 | 8/1992 | Ohmori et al. | 514/547 |
| 5,212,159 | 5/1993 | Ohmori et al. | 514/19 |
| 5,232,913 | 8/1993 | Ohmori et al. | 514/18 |

*Primary Examiner*—Raymond J. Henley, III

*Attorney, Agent, or Firm*—Wenderoth, Lind & Ponack

[57] ABSTRACT

A method of lowering lipids is disclosed wherein a patient is administered a lipid metabolism improving composition characterized by comprising a compound of the following formula:

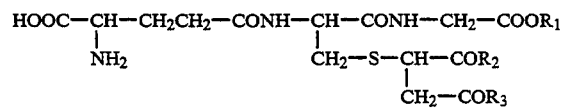

wherein $R_1$ represents a hydrogen atom or a lower alkyl group; $R_2$ and $R_3$ are the same or different and each represents a hydroxyl group, a lower alkoxy group or an amino group, or a pharmacologically acceptable salt thereof as an active ingredient.

Since the compound of the present invention lowers blood triglyceride, cholesterol and $\beta$-lipoprotein levels, it is of value for ameliorating hyperlipidemia in arteriosclerotic diseases, e.g. myocardinal infarction, angina pectoris, cerebral infarction, cerebral arteriosclerosis, etc., nephrosis, hypertension, diabetes, obesity and other diseases, and prevention of various circulatory diseases.

5 Claims, No Drawings

METHOD OF LOWERING LIPIDS

BACKGROUND OF THE INVENTION

1. Field of the Invention

The present invention relates to a useful lipid metabolism improving composition. More particularly, the invention relates to a useful lipid metabolism improving composition comprising S-($\alpha$, $\beta$-dicarboxyethyl)-glutathione, which is a physiological substance, an ester or amide derivative thereof, or a pharmacologically acceptable salt thereof as an active ingredient.

2. Description of the Prior Art

Hyperlipidemia is regarded a risk factor for arteriosclerosis. It is known that deposition of blood lipids, chiefly cholesterol, on the artery wall causes an arteriosclerotic lesion. Recent advances in research in this field have cast light on the fact that particularly an elevation of low density lipoproteins (LDL), among blood lipids, plays a major role in arteriogenesis and that high density lipoproteins (HDL) are an antiarteriosclerotic factor contributory to the removal and degradation of the cholesterol taken up in the vascular wall and cell membrane and thus inhibitory to arteriogenesis.

Accordingly for the treatment and prevention of hyperlipidemia of various etiologies and arteriosclerosis and other diseases arising from hyperlipidemia, much work is underway for developing blood cholesterol lowering drugs and particularly drugs capable of reducing the blood level of low density lipoproteins and increasing that of high density lipoproteins.

However, the state of the art has so far failed to provide a fully satisfactory drug.

Under the circumstances the inventors of the present invention explored in earnest for compounds having potent lipid metabolism improving activity and found that S-($\alpha$, $\beta$-dicarboxyethyl)glutathione, which is a physiological substance, and its ester and amide derivatives have a strong lipid metabolism improving action. Based on the above finding, the present invention has been completed.

SUMMARY OF THE INVENTION

The present invention is, therefore, directed to a lipid metabolism improving composition characterized by comprising a compound of the following formula:

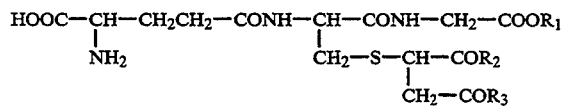

wherein $R_1$ represents a hydrogen atom or a lower alkyl group; $R_2$ and $R_3$ are the same or different and each represents a hydroxyl group, a lower alkoxy group or an amine group, or a pharmacologically acceptable salt thereof (hereinafter referred to briefly as the Compound) as an active ingredient.

DETAILED DESCRIPTION OF THE INVENTION

Among those active ingredient compounds which can be used in the lipid metabolism improving composition of the invention, S-($\alpha$, $\beta$-dicarboxyethyl)glutathione is a physiological substance discovered by D. H. Calam and S. G. Waley in the bovine crystalline lens (Biochem. J.86 226, 1963). The inventors of the present invention already discovered that this substance has blood coagulation inhibitory, platelet aggregation inhibitory, antiinflammatory-antiallergic, antitumor, and hepatic impairment inhibitory activities (JPA Kokai S-63-8337, JPA Kokai H-2-255624, JPA Kokai H-3-48626, JPA Kokai H-3-112933 and JPA Kokai H-3-118334).

However, it has not heretofore been known that the Compound has lipid metabolism improving activity.

Referring to the above formula, $R_1$ represents a hydrogen atom or a lower alkyl group. As to the alkyl group, the preferred number of carbon atoms is 1 to 10 and its carbon chain may be linear, branched or cyclic and may contain a ring moiety. As such, the alkyl group included, among others, methyl, ethyl, n-propyl, i-propyl, cyclopropyl, n-butyl, t-butyl, sec-butyl, n-pentyl, 1-ethylpropyl, i-pentyl and benzyl.

Referring, further, to the above formula, $R_2$ and $R_3$ are the same or different and each represents a hydroxyl group, a lower alkoxy group or an amino group. As to the alkoxy group, the preferred number of carbon atoms is 1 to 10 and its carbon chain may be linear, branched or cyclic and may contain a ring moiety. As examples of such alkoxy group may be mentioned methoxy, ethoxy, propoxy, isopropoxy, butoxy, isobutoxy, sec-butoxy, tert-butoxy, pentyloxy, isopentyloxy, tert-pentyloxy, neopentyloxy, 2-methylbutoxy, 1,2-dimethylpropoxy and 1-ethylpropoxy.

In the lipid metabolism improving composition of the present invention, the Compound may occur either as the free acid or in the form of a pharmacologically acceptable salt, such as an alkali metal salt, e.g. sodium salt, potassium salt, etc., or an alkaline earth metal salt, e.g. calcium salt, magnesium salt and so on. These salts may be those involving all the carboxyl groups available in the compound or those involving fewer of the carboxyl groups. The available number of salt-forming carboxyl groups in the present compound varies according to the type of salt and production pH. However, all of them can be used with advantage in the production of the pharmaceutical composition of the invention.

The lipid metabolism improving composition of the present invention may contain one or more species of the Compound in suitable combination according to the object and need.

The Compound for use as the active ingredient of the lipid metabolism improving composition of the invention can be produced by the known method, for example by the following alternative processes. Since S-($\alpha$, $\beta$-dicarboxyethyl)glutathione is present in yeasts and the bovine lens, among others, it can be isolated from such sources by known extraction and purification procedures. As to synthetic production, S-($\alpha$, $\beta$-dicarboxyethyl)glutathione can be synthesized from glutathione by allowing an equimolar mixture of glutathione and maleic acid to react in aqueous or alcoholic aqueous solution at an elevated temperature or room temperature for 1 to 2 days. The use of a maleic acid mono(or di)ester or a maleic acid mono(or di)amide in lieu of maleic acid in the like manner yields the corresponding S-($\alpha$, $\beta$-dicarboxyethyl)glutathione ester or amide derivative. Since all of these compounds have asymmetric carbon atoms within the molecule, there exist optical isomers. Such optically active compounds and various mixtures thereof can all be used with success for purposes of the present invention.

The Compound, which is used as the active ingredient of the lipid metabolism improving composition of the present invention, is either a physiological substance or an ester or amide derivative thereof and, therefore, as is clear from Experimental Example 4 which appears hereinafter, has a very low toxicological potential and is highly safe so that it can be used with advantage in various dosage forms for the purpose of improving lipid metabolism.

Since the lipid metabolism improving composition of the present invention lowers blood triglyceride, cholesterol and $\beta$-lipoprotein levels, it is of value for ameliorating hyperlipidemia in arteriosclerotic diseases, e.g. myocardinal infarction, angina pectoris, cerebral infarction, cerebral arteriosclerosis, etc., nephrosis, hypertension, diabetes, obesity and other diseases, and for the prevention of various circulatory diseases.

The lipid metabolism improving composition of the present invention can be administered orally or by any other suitable route for the prevention and treatment of hyperlipidemia and arteriosclerosis and other diseases arising from hyperlipidemia. Suitable dosage forms include solid preparations such as tablets, granules, powders, capsules, etc. and liquid preparations such as injections, all of which can be manufactured by the established pharmaceutical procedures. These preparations may contain conventional excipients such as the binder, disintegrator, thickener, dispersant, reabsorption promoter, corrigent, buffer, surfactant, solubilizer, preservative, emulsifier, isotonizing agent, stabilizer, pit-adjusting agent, etc. in suitable proportions.

The dosage of the Compound for achieving the object of the present invention depends on a variety of factors such as the patient's age and body weight, dosage form, clinical conditions to be treated. However, taking an injectable preparation as an example, the recommended dosage for an adult is about 1 to 100 mg, which is to be administered once a day. In the case of an oral preparation, it is recommendable to administer about 10 to 1000 mg adult a few times a day.

Unless contrary to the object of the present invention, the lipid metabolism improving composition of the invention can be supplemented with other lipid metabolism improving agents and/or other active ingredients having different kinds of efficacies.

EXAMPLES

The following experimental and working examples are intended to describe the invention in further detail.

Experimental Example 1

Effect of the Compound on rat hypertriglyceridemia (Method)

Male Wistar rats, 7 weeks old, were used in fasted state.

Intralipid (Otsuka Pharmaceutical Co., Ltd.) was used for induction of hypertriglyceridemia in rats.

The experiment was performed in a control group, drug treatment groups and a normal group, each consisting of 8 to 9 animals.

The treatment groups were intraperitoneally dosed with glutathione (hereinafter referred to as GSH), S-(diethyl $\alpha$, $\beta$-dicarboxyethyl)glutathione (hereinafter, DCE-Et-GS), S-(diethyl $\alpha$, $\beta$-dicarboxyethyl)glutathione isopropyl ester (hereinafter, DCE-Et-GS-iPr) and S-($\alpha$, $\beta$-dicarbamoylethyl)glutathione (hereinafter, DCE-NH$_2$-GS), each dissolved in physiological saline. The dose was invariously 200 mg/2 ml/kg. The control group received 2 ml/kg of physiological saline i.p. The normal group was also provided.

Intralipid 2 ml/kg was injected into the tail vein 0.5 hour after administration of the test substance. Thirty minutes after the injection, the blood was collected and the serum triglyceride (TG) was determined.

(Results)

The results are shown in Table 1.

TABLE 1

| Effect on rat hypertriglyceridemia | |
|---|---|
| Group | TG (mg/dl) |
| Control | 118.5 ± 16 |
| DCE-Et-GS | 57.7 ± 4** |
| DCE-Et-GS-iPr | 66.1 ± 11* |
| DCE-NH$_2$-GS | 72.4 ± 6* |
| GSH | 150.4 ± 12 |
| Normal | 87.9 ± 2 |

Each value represents the mean ± S.E. n = 8–9.
Significant difference from control: *$p < 0.05$, **$p < 0.01$.

Significant triglyceride (TG) lowering effects were found in the DCE-Et-GS, DCE-Et-GS-iPr and DCE-NH$_2$-GS groups.

Experimental Example 2

Effect of the Compound on rat alcoholic fatty liver (Method)

Male Wistar rats, 7 weeks old, were used in fasted state.

The experiment was performed in a control group, drug treatment groups and a normal group, each consisting of 8 to 9 animals.

The treatment groups were orally dosed with GSH and DCE-Et-GS-iPr, each dissolved in distilled water, at the dose level of 1000 mg/5 ml/kg. The control group received 5 ml/kg of distilled water p.o. The normal group was also provided.

One hour after administration of the test substance, 10 ml/kg of 38% ethyl alcohol was orally administered to the animals for induction of fatty liver. The liver was excised 6 hours after administration of ethyl alcohol and the triglyceride (TG) was determined by the acetylacetone method.

(Results)

The results are shown in table 2.

TABLE 2

| Effect on rat alcoholic fatty liver | |
|---|---|
| Group | TG (mg/g liver) |
| Control | 13.8 ± 0.3 |
| DCE-Et-GS-iPr | 10.7 ± 0.3* |
| GSH | 13.0 ± 0.4 |
| Normal | 12.6 ± 0.4 |

Each value represents the mean ± S.E. n = 8–9.
Significant difference from control: *$p < 0.001$.

A significant triglyceride (TG) lowering effect was found in the DCE-Et-GS-iPr group.

Experimental Example 3

Effect of the Compound on rat streptozotocin diabetes (Method)

The experiment was performed in a control group, drug treatment groups and a normal group, each consisting of 6 to 7 animals.

Using male 4-week-old SD rats, streptozotocin (STZ), 70 mg/kg, was injected into the tail vein to construct a diabetes model. As test substances, DCE-GS, DCE-Et-GS and DCE-Et-GS-iPr, each dissolved in physiological saline, were respectively administered intraperitoneally in doses of 100 mg/2 ml/kg once a day. The control group received physiological saline, 2 ml/kg, i.p. The normal group was also provided.

At weeks 4 and 8 of treatment, the blood was collected from the tail and the total cholesterol was determined. Furthermore, at week 10, the blood was collected from the abdominal aorta for blood biochemical tests.

(Results)

The results are shown in Tables 3 and 4.

TABLE 3

Effect on blood total cholesterol

| Group | Total Cholesterol (mg/dl) | | |
|---|---|---|---|
| | Week 4 | Week 8 | Week 10 |
| Control | 149.6 ± 24 | 189.2 ± 17 | 142 ± 11 |
| DCE-GS | 109.8 ± 12* | 118.2 ± 15* | 95 ± 6* |
| DCE-Et-GS | 117.2 ± 15* | 122.1 ± 17* | 95 ± 17* |
| DCE-Et-GS-iPr | 113.9 ± 16** | 110.5 ± 14** | 120 ± 10 |
| Normal | 53.2 ± 8 | 78.1 ± 5 | 80 ± 6 |

Each value represents the mean ± S.E. n = 4–7.
Significant difference from control: *p < 0.05, **p < 0.01.

TABLE 4

Effect on blood triglycerides, β-lipoproteins and VLDL

| Group | TG (mg/dl) | β-lipoproteins (mg/dl) | VLDL (mg/dl) |
|---|---|---|---|
| Control | 1045 ± 215 | 1825 ± 366 | 909 ± 389 |
| DCE-GS | 406 ± 86* | 759 ± 154* | — |
| DCE-Et-GS | 248 ± 69* | 518 ± 141* | — |
| DCE-Et-GS-iPr | 404 ± 86** | 818 ± 163* | 106 ± 52+ |
| Normal | 75 ± 8 | 126 ± 12 | — |

Each value represents the mean ± S.E. n = 4–7.
Significant difference from control: *p < 0.05, +0.1 > p > 0.05.

It is apparent from Table 3 that the Compound showed a significant blood total cholesterol lowering effect.

It is apparent from Table 4 that triglyceride (TG) and β-lipoprotein levels at week 10 were significantly decreased, indicating a relief of symptoms. In streptozotocin-diabetic rats the depressed lipoprotein lipase activity (LPL) causes a delay of very-low-density lipoprotein (VLDL) catabolism and this delayed catabolism prevails over the synthesis and release thereof in the liver to cause an absolute increase in VLDL. However, the lipoprotein fraction indicated a decrease in VLDL and a marked amelioration of TG-rich lipoprotein abnormality was found.

Experimental Example 4

Intravenous acute toxicity study

Using male ddY mice weighing about 20 g in groups of 5, an intravenous acute toxicity study was conducted using DCE-GS. The dose levels were 100, 200 and 400 mg/kg (common ratio 2). The injection for intravenous administration was adjusted to pit 7 with 1N-sodium hydroxide. During the 72-hour observation period, neither death nor abnormal behaviors were observed.

Example 1 Oral tablet

| S-(Diethyl α,β-dicarboxyethyl)glutathione isopropyl ester | 100 mg |
|---|---|
| Lactose | 80 mg |
| Starch | 17 mg |
| Magnesium stearate | 3 mg |

Using the above materials per tablet, oral tablets are manufactured by the established pharmaceutical procedure. If necessary, the tablets may be sugar-coated.

Example 2 Injection

| S-(α,β-dicarboxyethyl)glutathione sodium | 1.5 g |
|---|---|
| Sodium chloride | 0.6 g |
| Distilled water for injection | 100 ml |

The above materials are blended and sterilized by filtration. The filtrate is distributed in 2 ml portions into glass ampoules which are then sealed by fusing to provide injection products.

What is claimed is:

1. A method for lowering triglyceride, total cholesterol, β-lipoprotein or very-low density lipoprotein in blood which comprises administering to a human in need of such lowering a triglyceride-, total cholesterol-, β-lipoprotein- or very-low density lipoprotein-lowering effective amount of a compound of the following formula:

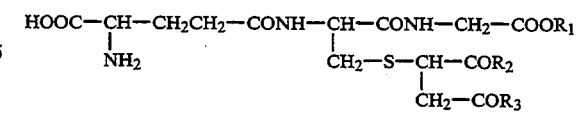

wherein $R_1$ represents a hydrogen atom or a lower alkyl group; $R_2$ and $R_3$ are the same or different and each represents a hydroxyl group, a lower alkoxy group or an amino group, or a pharmacologically acceptable salt thereof.

2. A method according to claim 1 wherein the compound is S-(α,β-dicarboxyethyl)glutathione.

3. A method according to claim 1 wherein the compound is S-(diethyl α,β-dicarboxyethyl)glutathione.

4. A method according to claim 1 wherein the compound is S-(diethyl α,β-dicarboxyethyl)glutathione isopropyl ester.

5. A method according to claim 1 wherein the compound is S-(α,β-dicarbamoylethyl)glutathione.

* * * * *